United States Patent [19]
Halloran

[11] Patent Number: 6,147,038
[45] Date of Patent: Nov. 14, 2000

[54] OPTICALLY CLEAR HAIR CONDITIONING COMPOSITIONS CONTAINING AMINOFUNCTIONAL SILICONE MICROEMULSIONS

[75] Inventor: Daniel Joseph Halloran, Midland, Mich.

[73] Assignee: Dow Corning Corporation, Midland, Mich.

[21] Appl. No.: 09/122,256

[22] Filed: Jul. 24, 1998

Related U.S. Application Data

[63] Continuation-in-part of application No. 07/705,455, May 24, 1991, Pat. No. 5,093,005.

[51] Int. Cl.[7] .................................. C11D 1/38; C11D 3/02
[52] U.S. Cl. .................. 510/122; 510/121; 510/123; 510/124; 510/466; 510/135; 510/137; 510/151; 510/471; 510/423
[58] Field of Search ........................... 510/121, 122, 510/123, 124, 466, 135, 137, 151, 471, 473; 427/70.12, 70.13

[56] References Cited

U.S. PATENT DOCUMENTS

| | | | |
|---|---|---|---|
| 2,781,354 | 2/1957 | Mannheimer | 548/352.1 |
| 4,275,055 | 6/1981 | Nachtigal | 424/70.19 |
| 4,374,125 | 2/1983 | Newell | 424/70 |
| 4,387,090 | 6/1983 | Bolich | 424/70.12 |
| 4,559,227 | 12/1985 | Chandra | 510/122 |
| 4,563,347 | 1/1986 | Starch | 424/70.12 |
| 4,586,518 | 5/1986 | Cornwall | 424/70.12 |
| 4,601,902 | 7/1986 | Fridd | 424/70.122 |
| 4,618,689 | 10/1986 | Traver | 424/70.12 |
| 4,620,878 | 11/1986 | Gee | 106/287.15 |
| 4,733,677 | 3/1988 | Gee | 424/70.12 |
| 4,749,732 | 6/1988 | Kohl et al. | 524/43 |
| 4,788,006 | 11/1988 | Bolich | 510/121 |
| 4,933,176 | 6/1990 | Reeth | 424/70.121 |
| 4,997,461 | 3/1991 | Harnett et al. | 51/295 |
| 5,049,377 | 9/1991 | Lamb et al. | 424/70.121 |
| 5,063,044 | 11/1991 | Kohl | 424/47 |
| 5,077,040 | 12/1991 | Bergmann et al. | 424/70.122 |
| 5,087,443 | 2/1992 | Chizat | 424/70.121 |
| 5,108,738 | 4/1992 | Halloran et al. | 424/70.14 |
| 5,126,126 | 6/1992 | Varpath | 424/70.12 |
| 5,132,443 | 7/1992 | Traver et al. | 556/425 |
| 5,145,607 | 9/1992 | Rich | 252/547 |
| 5,152,914 | 10/1992 | Foster et al. | 252/174 |
| 5,160,449 | 11/1992 | Halloran | 510/418 |
| 5,240,698 | 8/1993 | Traver et al. | 427/71 |
| 5,326,483 | 7/1994 | Halloran | 252/174.15 |
| 5,578,298 | 11/1996 | Berthiaume et al. | 424/70.122 |
| 5,679,331 | 10/1997 | Hague | 424/70.19 |
| 5,747,436 | 5/1998 | Patel et al. | 510/124 |
| 5,776,871 | 7/1998 | Cothran et al. | 512/122 |
| 5,856,544 | 1/1999 | Czech et al. | 552/425 |

OTHER PUBLICATIONS

Dow Corning Corp. Corporate Test Method CTM0851. "Turbidity of Liquids by Light Scattering." Jun. 17,.
Dow Corning Corp. Corporate Test Method CTM 0004. "Viscosity–Glass Capillary Viscometer." Jul. 29, 1970.
Schwartz et al. "Surface Active Agents–Their Chemistry & Technology." 1949, Chapters 7 & 8.
"McCutcheon's Emulsifiers & Detergents." North American Edition, 1989, pp. 257 & 258.
Schwartz et al. "Surface Active Agents & Detergents." 1977, vol. II, Chapters 4.

*Primary Examiner*—Kery Fries
*Attorney, Agent, or Firm*—Timothy J. Troy

[57] ABSTRACT

This invention relates to the use of aminofunctional silicone microemulsions to make optically clear hair conditioning compositions. More particularly this invention is directed to optically clear hair conditioning compositions comprising an aminofunctional microemulsion, at least one long-chain quaternary amine salt, and water. The optically clear silicone compositions of this invention are useful in the hair care industry, especially as hair conditioners.

15 Claims, No Drawings

OPTICALLY CLEAR HAIR CONDITIONING COMPOSITIONS CONTAINING AMINOFUNCTIONAL SILICONE MICROEMULSIONS

CROSS REFERENCE TO RELATED APPLICATIONS

This is a continuation-in-part of Ser. No. 07/705,455, filed on May 24, 1991 U.S. Pat. No. 5,093,005.

FIELD OF THE INVENTION

This invention relates to the use of aminofunctional silicone microemulsions to make optically clear hair conditioning compositions. More particularly this invention is directed to an optically clear hair conditioning composition comprising an aminofunctional silicone microemulsion and at least one long-chain dialkyl quaternary amine salt.

BACKGROUND OF THE INVENTION

It is desirable to provide compositions which have beneficial effects on wet and dry hair, for example which improve handle, softness, silkiness, and ease of combing the hair. Such beneficial effects may be obtained by incorporating certain types of silicones into hair care compositions. The preferred silicones include alkyl- or aryl-functional polydiorganosiloxanes. However, such compounds are not easily incorporated and result in opaque or at best translucent hair care products. It is aesthetically desirable to provide optically clear hair care compositions.

Silicones in hair care compositions have been disclosed in a number of different publications. For example, in U.S. Pat. No. 4,788,006 is disclosed shampoo compositions which comprise a synthetic, anionic surfactant, a dispersed, insoluble, non-volatile silicone, a xanthan gum suspending agent and water.

Hair treating compositions containing aminofunctional polysiloxanes have also been described. For example, in U.S. Pat. No. 4,563,347 it is disclosed that an aqueous emulsion of aminoalkyl substituted polydimethylsiloxane is useful to condition hair because it facilitates combing and imparts a smooth feel to hair. The aminoalkyl substituents are credited with providing the copolymers with cationic sites that make the polymer more substantive to hair than nonsubstituted polydimethylsiloxane. The '347 patent further teaches the use of aminofunctional polydiorganosiloxane solutions and emulsions as conditioners. Other hair treating compositions containing amino functional polysiloxanes are described in U.S. Pat. Nos. 4,586,518, 4,601,902, and 4,618,689, however these references do not describe the use of microemulsions in these compositions.

Aminofunctional microemulsions have also been described in the art. For example, in U.S. Pat. No. 4,749,732 is disclosed the use polydiorganosiloxanes containing aminoalkyl groups modified by alkoxycarbonylalkyl substituents in hair care compositions. The '732 patent also teaches that the modified aminoalkyl silicones exhibit improved deposition on hair and can be formulated into shampoos or conditioners. The '732 patent states that microemulsions of modified aminoalkyl substituted polydiorganosiloxane can be prepared by the method described in U.S. Pat. No. 4,620,878 which describes generally the preparation of microemulsions of aminofunctional silicones. The '732 patent does not disclose how to prepare these modified aminoalkyl substituted polydiorganosiloxane microemulsions. Further the '732 patent does not disclose an unmodified or unsubstituted amino functional microemulsion as an ingredient in an optically clear silicone formulation. In addition, these modified amino substituted microemulsions utilize acrylic monomers which give rise to serious odor problems making the materials unsuitable for cosmetic use.

In U.S. Pat. No. 4,559,227 a conditioning shampoo composition is taught containing a nonionic surfactant of the alkanolamide or amine oxide type, an aminofunctional polydiorganosiloxane as a hair conditioning component, a detersive surfactant of the anionic or amphoteric type, and water, the shampoo composition being in the form of an aqueous solution. The '227 patent further discloses a method of preparing the shampoo composition as a stable solution. This is in contrast to this invention which employs pre-made microemulsions as opposed to solutions as components to provide optically clear silicone compositions. The use of the premade microemulsion allows an easier to use shampoo to be formed without a complex premixing of the composition.

Polydiorganosiloxane microemulsions have also been described in the hair care art. For example, European Patent Publication No. 268,982 discloses cosmetic compositions containing microemulsions of dimethylpolysiloxanes produced by emulsion polymerization which provide long term storage stability. However, the formulations of the '982 application do not disclose a aminofunctional silicone microemulsion as an ingredient in an optically clear silicone composition that provides substantive conditioning.

In U.S. Pat. No. 5,063,044 is disclosed a hair conditioning composition being a mixture including water, a thickener, and an organosilicon compound. The organosilicone compound can take the form of a microemulsion and is selected from the group consisting of carboxy glycol ether and carboxy-glycol ester functional polysiloxanes, which are appreciably polar and soluble molecules. In contrast, this invention utilizes a non-polar insoluble aminofunctional polydiorganosiloxane microemulsion in combination with certain materials to unexpectedly provide true optical clarity to the silicone compositions of this invention along with robust, substantive conditioning when applied to hair.

This invention can therefore be distinguished from the references enumerated above in that this invention contains a aminofunctional silicone microemulsion in combination with certain materials to provide truly optically clear hair conditioning compositions that have beneficial effects greater than the hair conditioning formulations known in the art.

SUMMARY OF THE INVENTION

This invention is directed to an optically clear hair conditioning composition comprising an aminofunctional silicone microemulsion, at least one long-chain dialkyl quaternary amine salt, and water.

The hair conditioning compositions of this invention are optically clear, easy to use, have outstanding conditioning, and are easy to formulate.

While not limiting this invention to any particular theory, it is believed that the microemulsion must contain a siloxane with amino-functionality to allow a truly optically clear silicone composition to be formed. It is believed that the amino group functions both to give clear systems and to give substantive conditioning. The clarity is believed to be achieved through improved interfacial tension reduction due to the presence of the amino groups.

DETAILED DESCRIPTION OF THE INVENTION

This invention relates to an optically clear hair conditioning composition comprising (A) an aminofunctional silicone microemulsion having an average particle size of less than 0.06 microns, (B) at least one long-chain dialkyl quaternary amine salt, and (C) water.

For the purposes of this invention, the term "optically clear" is used to define a composition that is transparent (transmitting light without distortion) which means that the size of the particles in the composition are reduced to a size where they are not observable with optical (visual) means. According to this invention, "optically clear" is further defined by NTU's (Nephelometric Turbidity Units), which is the unit of measure for the turbidity or haze of a liquid. NTU's range from 0.04 to 1,000 or higher. A more detailed description of this test is found hereinbelow. The haze value of a relatively turbid solution is about 100 NTU's or higher, and mixtures with a slight haze give values of 20 to 50 NTU's. In contrast the compositions of this invention have an average haze value of 3 to 5 NTU's.

Component (A) is an aminofunctional silicone microemulsion having an average particle size of less than 0.06 microns. Microemulsions are mixtures of oil and water where the particle size of the resulting droplets is small enough so the resulting mixture is clear or translucent. Because of their relative clarity microemulsions are distinguishable from standard opaque emulsions in that certain microemulsions can be used to prepare clear cosmetics. The clarity of these compositions is advantageous in cosmetic applications such as in the hair care art. Microemulsions are also more temperature, dilution, and formulation stable than standard emulsions. Microemulsion droplet sizes are variously defined in the chemical art with an upper limit on the droplet size typically being placed somewhere between 0.10 and 0.15 micron to distinguish microemulsions from opaque standard emulsions. In general, microemulsions can also be defined by their appearance: microemulsions are transparent or translucent, and do not display the opalescence of standard emulsions. While microemulsions with average droplet sizes between 0.10 and 0.15 micron display the properties of microemulsions, microemulsions with average droplet sizes less than 0.06 micron are especially preferred for their even greater clarity and stability.

The aminofunctional microemulsions of this invention comprise (i) an aminofunctional polyorganosiloxane, (ii) at least one surfactant, and (iii) water.

Preferably the aminofunctional polyorganosiloxane of (A)(i) of this invention is a compound having its formula selected from the group consisting of $R^2R_2SiO(R_2SiO)_a(R^1RSiO)_bSiR_2R^2$ and
$R^2R_2SiO(R_2SiO)_a(R^1SiO_{3/2})_bSiR_2R^2$ wherein R is a monovalent hydrocarbon radical, $R^1$ is an aminoalkyl group having its formula selected from the group consisting of —$R^3NH_2$ and —$R^3NHR^4NH_2$ wherein $R^3$ is a divalent hydrocarbon radical having at least 3 carbon atoms and $R^4$ is a divalent hydrocarbon radical having at least 2 carbon atoms, $R^2$ is selected from the group consisting of R, $R^1$, and —OH, a has a value of 0 to 2000, and b has a value of from greater than zero to 200.

The monovalent R radicals are exemplified by alkyl radicals such as the methyl, ethyl, propyl, butyl, amyl, and hexyl, alkenyl radicals such as the vinyl, allyl, and hexenyl, cycloalkyl radicals such as the cyclobutyl and cyclohexyl, aryl radicals such as the phenyl and naphthyl, aralkyl radicals such as the benzyl and 2-phenylethyl, alkaryl radicals such as the tolyl, and xylyl, halohydrocarbon radicals such as 3-chloropropyl, 4-bromobutyl, 3,3,3-trifluoropropyl, chlorocyclohexyl, bromophenyl, and chlorophenyl. It is preferred that R is a monovalent hydrocarbon radical having from 1 to 6 carbon atoms. Especially preferred R radicals are methyl, phenyl, and vinyl.

The group $R^3$ is preferably an alkylene radical having from 3 to 20 carbon atoms. Preferably $R^3$ is selected from the group consisting of propylene, —$CH_2CHCH_3$—, butylene, —$CH_2CH(CH_3)CH_2$—, pentamethylene, hexamethylene, 3-ethyl-hexamethylene, octamethylene, and decamethylene.

The group $R^4$ is preferably an alkylene radical having from 2 to 20 carbon atoms. Preferably $R^4$ is selected from the group consisting of ethylene, propylene, —$CH_2CHCH_3$—, butylene, —$CH_2CH(CH_3)CH_2$—, pentamethylene, hexamethylene, 3-ethyl-hexamethylene, octamethylene, and decamethylene.

It is highly preferred in this invention that $R^1$ is selected from the group consisting of —$CH_2CH_2CH_2NHCH_2CH_2NH_2$ and —$CH_2CH(CH_3)CH_2NHCH_2CH_2NH_2$.

Salts of these same aminofunctional radicals may also be used in this invention. Examples of such salts include alkyl carboxylate salts, aryl carboxylate salts, halide salts such as chlorides and bromides, and other neutralization products of the amines with organic acids.

Although the group $R^2$ can be selected from the group consisting of R, $R^1$, and —OH, it is preferred for purposes of this invention that $R^2$ is methyl or —OH.

It is preferred that the polyorganosiloxanes have from about 0.1 to 15 molar percent of the above described amino groups and most preferably from about 0.2 to 10 molar percent of the above described amino groups. In the above formulas, preferably a has a value of from 50 to 2000, and b has a value of 1 to 100. The aminofunctional polyorganosiloxanes useful in the this invention can be prepared by procedures well known in the art. Many of these polyorganosiloxanes are available commercially. Therefore their preparation will not be described here.

The microemulsion of component (A) also comprises (ii) at least one surfactant. The surfactant may be an anionic, cationic, nonionic, or amphoteric surfactant. The surfactants may be employed separately or in combinations of two or more.

Examples of suitable anionic surfactants include alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, alkylbenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristylbenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid.

Examples of cationic surfactants include various fatty acid amines and amides and their derivatives, and the salts of the fatty acid amines and amides. Examples of aliphatic fatty acid amines include dodecylamine acetate, octadecylamine acetate, and acetates of the amines of tallow fatty acids, homologues of aromatic amines having fatty acids such as dodecylanalin, fatty amides derived from aliphatic diamines such as undecylimidazoline, fatty amides derived from aliphatic diamines such as undecylimidazoline, fatty amides derived from disubstituted amines such as oleylaminodiethylamine, derivatives of ethylene diamine, quaternary ammonium compounds and their salts which are exemplified by tallow trimethyl ammonium chloride, dioctadecyldimethyl ammonium chloride, didodecyldimethyl ammonium chloride, dihexadecyl ammonium chloride, alkyltrimethylammonium hydroxides such as octyltrimethylammonium hydroxide, dodecyltrimethylammonium hydroxide, or hexadecyltrimethylammonium hydroxide, dialkyldimethylammonium hydroxides such as octyldimethylammonium hydroxide, decyldimethylammonium hydroxide, didodecyldimethylammonium hydroxide, dioctadecyldimethylammonium hydroxide, tallow trimethylammonium hydroxide, coconut oil, trimethylammonium hydroxide, methylpolyoxyethylene cocoammonium chloride, and dipalmityl hydroxyethylammonium methosulfate, amide derivatives of amino alcohols such as betahydroxylethylstearylamide, and amine salts of long chain fatty acids.

Examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxane surfactants.

Examples of the amphoteric surfactants that can be used include amino acid surfactants and betaine acid surfactants. Combinations of 2 or 3 types of nonionic surfactants, combinations of nonionic surfactants and anionic surfactants, and combinations of nonionic surfactants and cationic surfactants can also be employed as component (A)(ii).

Preferred surfactants as component (A)(ii) include trimethylnonyl polyethylene glycol ethers and polyethylene glycol ether alcohols containing linear alkyl groups having from 11 to 15 such as 2,6,8-trimethyl-4-nonyloxypolyethylene oxyethanol (6 EO) (sold as Tergitol®TMN-6 by OSi Specialties, A Witco Company, Endicott, N.Y.), 2,6,8-trimethyl-4-nonyloxypolyethylene oxyethanol (10 EO) (sold as Tergitol®TMN-10 by OSi Specialties, A Witco Company, Endicott, N.Y.), alkyleneoxypolyethylene oxyethanol ($C_{11-15}$ secondary alkyl, 9 EO) (sold as Tergitol®15-S-9 by OSi Specialties, A Witco Company, Endicott, N.Y.), alkylene-oxypolyethylene oxyethanol ($C_{11-15}$ secondary alkyl, 15 EO) (sold as Tergitol®15-S-15 by OSi Specialties, A Witco Company, Endicott, N.Y.), octylphenoxy polyethoxy ethanols having varying amounts of ethylene oxide units such as octylphenoxy polyethoxy ethanol (40 EO) (sold as Triton® X405 by Rohm and Haas Company, Philadelphia, Pa.), nonionic ethoxylated tridecyl ethers available from Emery Industries, Mauldin, S.C. under the general tradename Trycol, alkali metal salts of dialkyl sulfosuccinates available from American Cyanamid Company, Wayne, N.J. under the general tradename Aerosol, polyethoxylated quaternary ammonium salts and ethylene oxide condensation products of the primary fatty amines, available from Armak Company, Chicago, Ill. under the tradenames Ethoquad, Ethomeen, or Arquad, and polyoxyalkylene glycol modified polysiloxanes. These preferred surfactants may also be obtained from other suppliers under different tradenames.

The surfactant(s) (A)(ii) should be present in the microemulsion of component (A) in an amount ranging from 0.1 to 250 parts by weight, and preferably 2 to 100 parts by weight per 100 parts by weight of aminofunctional organopolysiloxane component (A)(i).

Water, component (A)(iii) forms the remainder of microemulsion (A) in the optically clear hair conditioning compositions of this invention. There must be sufficient water present to form a transparent mixture. Generally water is present at a level of from about 10 to 900 parts by weight, preferably from about 80 to about 400 parts by weight per 100 parts by weight of aminofunctional organopolysiloxane (A)(i).

The microemulsions of this invention can be prepared by two different methods. The first is the mechanical method described in U.S. Pat. No. 4,620,878 issued Nov. 6, 1986, which is hereby incorporated by reference herein. The method involves forming a "translucent concentrate" of surfactant, aminofunctional polysiloxane, and water in select proportions. The "concentrate" is then rapidly dispersed in additional water to form the microemulsion. The second method by which the microemulsions of this invention are produced is described in European Patent No. 0459500, which teaches a method of producing oil free microemulsions by emulsion polymerization, the method comprising a mixture of at least one aminofunctional siloxane oligomer, cationic or anionic surfactant, nonionic surfactant, catalyst and water whereby the siloxane oligomer is reacted in the presence of water and the surfactants to form the polysiloxane microemulsions. It is further taught that although the order the ingredients are combined in is not critical, it is essential to have agitation during and following the addition of the ingredients and to have achieved or to heat to the polymerization temperature when all the ingredients have been combined.

The aminofunctional organopolysiloxane microemulsion (A) is present in the optically clear hair conditioning compositions of this invention in an amount from about 0.1 to 50 weight percent (wt %) and preferably about 2 to 10 wt % based on the total weight of the composition.

For the hair conditioning compositions to be optically clear the Cationic Equivalence of the microemulsions are preferably less than 0.15. For purposes of this invention, the term "Cationic Equivalence" is used to define the number of equivalents or milliequivalents (depending on the data source) of cationic functionality per gram of sample. It is critical to the compositions of this invention that a microemulsion be present to provide clear hair conditioning compositions.

Component (B) in the compositions of this invention is at least one long-chain dialkyl quaternary amine salt. Preferred dialkyl quaternary amine salts are those having the formula $(R^5R^6NR^7R^8)+•X^-$ wherein $R^5$ is selected from the group consisting of an aliphatic group having from 8 to 22 carbon atoms, an aromatic group having from 8 to 22 carbon atoms, an aryl group having from 8 to 22 carbon atoms, and an alkylaryl group having from 8 to 22 carbon atoms, $R^6$ is an aliphatic group having from 8 to 22 carbon atoms, $R^7$ and $R^8$ are each alkyl groups having from 1 to 3 carbon atoms, and X is an anion selected from halogen, acetate, phosphate, nitrate and alkylsulfate radicals. It is especially preferred that $R^5$ is selected from the group consisting of an aliphatic group having from 12 to 22 carbon atoms, an aromatic group having from 12 to 22 carbon atoms, an aryl group having from 12 to 22 carbon atoms, and an alkylaryl group having from 12 to 22 carbon atoms and $R^6$ is an aliphatic group having from 12 to 22 carbon atoms.

Preferred dialkyl quaternary amine salts are dialkyldimethylammonium chlorides wherein each alkyl group contains from 12 to 22 carbon atoms. Preferred dialkyl quaternary amine salts are exemplified by ditallow dimethyl ammonium chloride, ditallow dimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, stearyl dimethyl benzyl ammonium chloride, ditallow dimethyl ammonium chloride, dicetyl dimethyl ammonium chloride, stearyl dimethyl benzyl ammonium chloride, and dicoco dimethyl ammonium chloride.

The dialkyl quaternary amine salt, component (B), is preferably present in an amount of from about 0.1 to 5 wt % based on the total weight of the composition.

Water, component (C) forms the remainder of the optically clear hair conditioning compositions of this invention and is generally present at a level of from about 50 to 99 wt %, preferably from about 80 to about 99 wt % based on the total weight of the composition.

Other optional components may be added to the hair conditioning compositions of this invention such as fragrances, preservatives, and botanicals (plant extracts). The optional ingredients can be present in an amount of up to 5 parts by weight per 100 parts by weight of optically clear hair conditioning composition, but preferably are present in amount of from 0.1 to 1 part by weight per 100 parts by weight of optically clear hair conditioning composition.

The hair conditioning compositions of this invention may be in the form of a gel, paste, or a freely pourable liquid. The hair conditioning compositions of this invention can be used on the hair of humans or animals to cleanse and improve the appearance of their or coats, respectively. The hair conditioning compositions of this invention are expected to be used by the usual method of adding the hair conditioning composition to the hair, massaging the hair conditioning composition into the hair and removing the hair conditioning composition from the hair by rinsing with water.

The hair conditioning compositions may be prepared by simply mixing components (A)–(C) and any optional ingredients together, and stirring them thoroughly. Heat may be applied to improve the dispersion of the ingredients.

Polyquaternium-11 is a polyvinylpyrrolidone-polydimethylaminoethylmethacrylate dimethylsulfate quaternary ammonium salt. Cocamide DEA is coconut acid diethanolamide. Nonoxynol-4 is polyoxyethylene (4) nonyl phenyl ether.

EXAMPLES

Silicone Microemulsions

1. Silicone Microemulsion A is a translucent, cationic microemulsion having an average droplet size of 30 nm diameter. The microemulsion was prepared by emulsion polymerization (the method of European Patent No. 0459500 described hereinabove). The microemulsion contained about 27 weight percent (wt %) aminofunctional organopolysiloxane fluid having the formula $HOMe_2SiO(Me_2SiO)_x(MeRSiO)_ySiMe_2OH$ wherein R denotes the group $—(CH_2)_3NH_2$ and containing 2 mole percent (mol %) y units, about 3 wt % dimethylsiloxane cyclics, 4 wt % tallow trimethyl ammonium chloride, about 8 wt % C11–15 ethoxylated lauryl alcohol, and about 58 wt % water. The silicone microemulsion also contained a preservative (Chloromethyl Isothiazolin-3-One).

2. Silicone Microemulsion B is a translucent, cationic microemulsion having an average droplet size of 30 nm diameter. The microemulsion was prepared by emulsion polymerization (the method of European Patent No. 0459500 described hereinabove). The microemulsion contained about 27 wt % aminofunctional organopolysiloxane fluid having the formula $HOMe_2SiO(Me_2SiO)_x(MeRSiO)_ySiMe_2OH$ wherein R denotes the group $—(CH_2)_3NH(CH_2)_2NH_2$ and containing 2 mol % y units, about 3 wt % dimethylsiloxane cyclics, about 4 wt % tallow trimethylammonium chloride, about 8 wt % ethoxylated lauryl alcohol, and 58 wt % of water. The silicone microemulsion also contained a preservative (Chloromethyl Isothiazolin-3-One).

3. Silicone Microemulsion C is a transparent, nonionic microemulsion having an average droplet size of 30 nm diameter. The microemulsion was prepared by the mechanical method of U.S. Pat. No. 4,620,878 incorporated by reference hereinabove. The microemulsion contained about 14 wt % aminofunctional organopolysiloxane fluid having the formula $Me_3SiO(Me_2SiO)_x(MeRSiO)_ySiMe_3$ wherein R denotes the group $—CH_2CH(CH_3)CH_2NH(CH_2)_2NH_2$, x having a value of about 390 and y having a value of about 8, about 2 wt % dimethylsiloxane cyclics, about 3 wt % polyethoxylated decyl alcohol, about 3 wt % $CH_3(CH_2)_{12}O(EO)_nCH_2COOH$, about 0.3 wt % of triethanolamine, about 7 wt % octylphenoxy polyethoxy (40) ethanol (70 percent in water), and about 71 wt % water.

4. Silicone Microemulsion D is a transparent, nonionic microemulsion having an average droplet size of 30 nm diameter. The microemulsion was prepared by the mechanical method of U.S. Pat. No. 4,620,878 incorporated by reference hereinabove. The composition contains about 15 wt % aminofunctional organopolysiloxane fluid having the formula $Me_3SiO(Me_2SiO)_x(MeRSiO)_ySiMe_3$ wherein R denotes the group $—CH_2CH(CH_3)CH_2NH(CH_2)_2NH_2$, x having a value of about 96 and y having a value of about 2, about 2.5 wt % trimethyl nonyl polyethylene glycol ether, about 3.9 wt % $CH_3(CH_2)_{12}O(EO)_nCH_2COOH$, about 0.3 wt % triethanolamine, about 10 wt % octylphenoxy polyethoxy (40) ethanol (70 percent in water), and about 68 wt % water.

5. Silicone Microemulsion E is a transparent, anionic microemulsion having an average droplet size of 25 nm diameter. The microemulsion was prepared by emulsion polymerization (the method of European Patent No. 0459500 described hereinabove). The microemulsion contained about 18 wt % of a hydroxydimethylsiloxy-terminated polydimethylsiloxane having a viscosity of 20,000 cP, about 2 wt % of unpolymerized dimethylsiloxane cyclics, 7.7 wt % triethanolamine dodecylbenzene sulfonate, and 5.6 wt % of polyoxyethylene (40) octylphenyl ether, and 67wt % water. The silicone microemulsion also contained a preservative (Chloromethyl Isothiazolin-3-One).

6. Silicone Microemulsion F is a cloudy yellowish cationic microemulsion having an average droplet size of 65 nm diameter. The emulsion was prepared by emulsion polymerization (by the method of European Patent No. 0459500 described hereinabove). The microemulsion contained about 30 wt % hydroxydimethylsiloxy-terminated dimethylsiloxane-methylsilsesquioxane gel, about 1 wt % unpolymerized dimethylsiloxane cyclics, and 4.7 wt % of a secondary alcohol ethoxylate, and 10.3 wt % of Ethoquad T13 27W (an ethoxylated quaternary ammonium salt). The composition contained about 54 wt % water. The silicone microemulsion also contained a preservative (Chloromethyl Isothiazolin-3-One).

7. Silicone Microemulsion G is a clear to slightly yellowish cationic microemulsion having an average droplet size of 30 nm diameter. The emulsion was prepared by the emulsion polymerization of dimethylsiloxane cyclics and contained about 30 wt % hydroxydimethylsiloxy-terminated dimethylsiloxane-aminoethylaminopropylsilsesquioxane having the formula $HOMe_2SiO(Me_2SiO)_x(RSiO_{3/2})_ySiMe_2OH$ wherein R is a group having the formula $-(CH_2)_3NH(CH_2)_2NH_2$ having 99.4 mol % dimethylsiloxane groups and 0.6 mol % aminoethylaminopropylsilsesquioxane groups, about 5 wt % of unpolymerized dimethylsiloxane cyclics, about 5.8 wt % tallow trimethyl ammonium chloride, about 9.5 wt % of an ethoxylated nonyl alcohol, 48.4 wt % water, and 1 wt % sodium dihydrogen phosphate. The silicone microemulsion also contained a preservative (Chloromethyl Isothiazolin-3-One).

8. Silicone Microemulsion H is a transparent, nonionic microemulsion. The microemulsion was prepared by the mechanical method of U.S. Pat. No. 4,620,878 incorporated by reference hereinabove. The microemulsion contained about 20 wt % of an aminofunctional organopolysiloxane fluid having the formula $Me_3SiO(Me_2SiO)_x(MeRSiO)_ySiMe_3$ wherein R denotes the group $-CH_2CH(CH_3)CH_2NH(CH_2)_2NH_2$, x having a value of about 390 and y having a value of about 8, about 3 wt % of trimethyl nonyl polyethylene glycol ether, about 2 wt % of polyethylene glycol ether of a linear alcohol, about 0.4 wt % acetic acid, and about 74.6 wt % water.

Example I

The following Dip Bath compositions were then prepared from the above described microemulsions in combination with a long-chain dialkyl quaternary amine salt (denoted "Quat Salt" in Table I) and these compositions are described in Table I below.

TABLE I

| DIP BATH COMPOSITION | MICROEMULSION | QUAT. SALT |
|---|---|---|
| J | — | water |
| K | — | 0.4 wt % DDAC* |
| L | 2 wt % E | — |
| M | 2 wt % E | 0.4 wt % DDAC |
| N | 2 wt % F | 0.4 wt % DDAC |
| O | 2 wt % C | — |
| P | 2 wt % B | 0.4 wt % DDAC |
| Q | 2 wt % G | 0.4 wt % DDAC |
| R | 2 wt % A | 0.4 wt % DDAC |
| S | 2 wt % A | 0.4 wt % DDAC |
| T | 2 wt % C | 0.4 wt % DDAC |
| U | 2 wt % B | 0.4 wt % DDAC |
| V | 2 wt % C | 0.4 wt % Cocamide DEA |
| W | 2 wt % C | 0.4 wt % PQ-11* |
| X | 2 wt % C | 0.4 wt % Nonoxynol-4 |
| Y | 2 wt % C | 0.4 wt % Sodium Sulfate |

*DDAC denotes dicocodimethyl ammonium chloride
*PQ-11 denotes Polyquaternium-11

The above Dip Bath Compositions (J–Y) were then evaluated for hair conditioning by the method described hereinbelow. Two gram hair tresses, on tabs, were prepared, shampooed with a blank shampoo, dried, and then subjected to a 30 minute presoak in distilled water. Each tress was removed, the excess water was removed, and the turn was detangled and then re-tangled by dipping it into distilled water three times over 15 seconds. Excess water was again removed. Each tress was dipped into a 200 g base, with the test material diluted to 2 wt %, for 30 seconds. Each tress was removed, excess water removed, and rinsed for 30 seconds in 40° C. tap water. The excess water removed, detangling, and re-tangling steps were repeated. Each tress was rated for wet combing (wc), wet feel (wf), dry combing (dc), dry feel (df), and appearance after zero, five, and ten shampoo latherings. In the rating system, 1=best, and 5=worst. The results of these tests are detailed below in Table II.

TABLE II

| | SUBSTANTIVE CONDITIONING | | | | | | | | | | | |
|---|---|---|---|---|---|---|---|---|---|---|---|---|
| | Initial | | | | After 5 Shampoos | | | | After 10 shampoos | | | |
| Treatment | wc | wf | dc | df | wc | wf | dc | df | wc | wf | dc | df |
| J | 3 | 2.5 | 3 | 3 | 4 | 3 | 3.5 | 3 | 5 | 3 | 3.5 | 3 |
| K | 1.5 | 2 | 2 | 2.5 | 4 | 3 | 1.5 | 3 | 5 | 3 | 3 | 3 |
| L | 3 | 2.5 | 2 | 2 | 3 | 3 | 3 | 3 | 4.5 | 3 | 3 | 3 |
| M | 1 | 2 | 1 | 1.5 | 2 | 3 | 2 | 2.5 | 4.5 | 3 | 3 | 3 |
| N | 1 | 2 | 1 | 2 | 1 | 2 | 2.5 | 2.5 | 5 | 3 | 2.5 | 3 |
| O | 3.5 | 3 | 2.5 | 2.5 | — | — | — | — | — | — | — | — |
| P | 1.5 | 3 | 1.5 | 2.5 | — | — | — | — | — | — | — | — |
| Q | 1.5 | 2 | 1.5 | 2 | 2 | 2 | 1.5 | 2 | 2.5 | 3 | 2.5 | 3 |
| R | 1.25 | 2 | 1 | 2 | — | — | — | — | — | — | — | — |
| S | 1 | 2 | 1.5 | 1.5 | 1.25 | 2 | 1.5 | 2 | 1.5 | 2 | 1.75 | 2.5 |
| T | 1.5 | 3 | 1 | 2.5 | 1 | 2 | 1.25 | 2 | 1.5 | 2 | 1.5 | 2.5 |
| U | 1.5 | 2 | 1.5 | 2.5 | — | — | — | — | — | — | — | — |
| V | 3 | 3 | 2 | 2 | 3 | 2 | 2 | 2 | 2 | 2 | 3 | 2 |
| W | 1 | 2 | 2 | 2 | 3 | 2 | 2.5 | 2 | 3 | 1 | 3 | 2 |

TABLE II-continued

SUBSTANTIVE CONDITIONING

| Treatment | Initial | | | | After 5 Shampoos | | | | After 10 shampoos | | | |
|---|---|---|---|---|---|---|---|---|---|---|---|---|
| | wc | wf | dc | df | wc | wf | dc | df | wc | wf | dc | df |
| X | 2.5 | 3 | 1 | 2 | 2.5 | 2 | 2 | 2 | 3.5 | 2 | 2.5 | 2.5 |
| Y | 2.5 | 2 | 1 | 2 | 3 | 2 | 2.5 | 3 | 4 | 2 | 3 | 2.5 |

This example illustrates the benefit of substantive conditioning when a aminoalkyl functional microemulsion is used in combination with a long-chain quaternary amine salt.

In all cases, the aminofunctional microemulsion is preferred over the polydimethylsiloxane microemulsion which demonstrated no substantive conditioning even when combined with a long-chain quaternary amine salt. This example also shows the improvements gained when using aminofunctional microemulsions with a long-chain quaternary amine salt over using either ingredient alone.

That which is claimed is:

1. An optically clear hair conditioning composition comprising:
   (A) an aminofunctional silicone microemulsion having an average particle size of less than 0.14 microns comprising:
      (i) an aminofunctional polyorganosiloxane having its formula selected from the group consisting of
      $R_3SiO(R_2SiO)_x(RQSiO)_ySiR_3$ and
      $HOR_2SiO(R_2SiO)_x(RQSiO)_ySiR_2OH$
      wherein R, selected from the group consisting of aryl, alkyl, and alkenyl radicals, Q is a polar radical having the formula —R'NHR$^2$ wherein R' is a divalent linking group composed of carbon and hydrogen atoms having from 2 to 10 carbon atoms, and R$_2$ is selected from the group consisting of a hydrogen atom, alkyl radicals containing from 1 to 4 carbon atoms, and the —CH$_2$CH$_2$NH$_2$ radical, the value of y is at least one, and the sum of x+y is less than 500;
      (ii) a surfactant which is insoluble in the polyorganosiloxane; and
      (iii) water; and
   (B) at least one long-chain dialkyl quaternary amine salt; and
   (C) water.

2. A composition according to claim 1, wherein R is methyl, Q is a polar radical having the formula —R'NHCH$_2$CH$_2$NH$_2$, R' is selected from the group consisting of propylene, and —CH$_2$CH(CH$_3$)CH$_2$—.

3. A composition according to claim 1, wherein Q is selected from the group consisting of —CH$_2$CH$_2$CH$_2$NHCH$_2$CH$_2$NH$_2$ and —CH$_2$CH(CH$_3$)CH$_2$NHCH$_2$CH$_2$NH$_2$.

4. A composition according to claim 1, wherein (A)(ii) is selected from the group consisting of anionic surfactants, cationic surfactants, nonionic surfactants, amphoteric surfactants, combinations of 2 or more types of nonionic surfactants, combinations of nonionic surfactants and anionic surfactants, and combinations of nonionic surfactants and cationic surfactants.

5. A composition according to claim 4, wherein the anionic surfactants are selected from the group consisting of alkali metal sulforicinates, sulfonated glyceryl esters of fatty acids, salts of sulfonated monovalent alcohol esters, amides of amino sulfonic acids, sulfonated products of fatty acids nitriles, sulfonated aromatic hydrocarbons, condensation products of naphthalene sulfonic acids with formaldehyde, sodium octahydroanthracene sulfonate, alkali metal alkyl sulfates, ether sulfates having alkyl groups of 8 or more carbon atoms, alkylarylsulfonates having 1 or more alkyl groups having 8 or more carbon atoms, alkylbenzenesulfonic acid alkali metal salts, sulfuric esters of polyoxyethylene alkyl ether, alkylnaphthylsulfonic acid sodium salts, alkylnaphthylsulfonic acid potassium salts, and alkylnaphthylsulfonic acid amine salts.

6. A composition according to claim 4, wherein the cationic surfactants are selected from the group consisting of fatty acid amines, fatty acid amides, fatty acid amine salts, fatty acid amide salts.

7. A composition according to claim 4, wherein the nonionic surfactants are selected from the group consisting of polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, and polyoxyalkylene glycol modified polysiloxanes.

8. A composition according to claim 4, wherein the amphoteric surfactants are selected from the group consisting of amino acid surfactants and betaine acid surfactants.

9. A composition according to claim 1, wherein (A)(ii) is selected from the group consisting of 2,6,8-trimethyl-4-nonyloxypolyethylene oxyethanol, 2,6,8-trimethyl-4-nonyloxypolyethylene oxyethanol, alkyleneoxypolyethylene oxyethanol, octylphenoxy polyethoxy ethanols, nonionic ethoxylated tridecyl ethers, alkali metal salts of dialkyl sulfosuccinates, polyethoxylated quaternary ammonium salts, ethylene oxide condensation products of primary fatty amines, and polyoxyalkylene glycol modified polysiloxanes.

10. A composition according to claim 1, wherein (B) is a compound having the formula

wherein R$^5$ is selected from the group consisting of an aliphatic group having from 8 to 22 carbon atoms, an aromatic group having from 8 to 22 carbon atoms, an aryl group having from 8 to 22 carbon atoms, and an alkylaryl group having from 8 to 22 carbon atoms, R$^6$ is an aliphatic group having from 8 to 22 carbon atoms, R$^7$ and R$^8$ are each alkyl groups having from 1 to 3 carbon atoms, and X is an anion selected from halogen, acetate, phosphate, nitrate and alkylsulfate radicals.

11. A composition according to claim 1, wherein (B) is a dialkyldimethylammonium chloride wherein each alkyl group contains from 12 to 22 carbon atoms.

12. A composition according to claim 1, wherein (B) is selected from the group consisting of ditallow dimethyl ammonium chloride, ditallow dimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl) dimethyl ammonium chloride, stearyl dimethyl benzyl ammonium chloride, ditallow dimethyl ammonium chloride, dicetyl dimethyl ammonium chloride, stearyl dimethyl benzyl ammonium chloride, and dicoco dimethyl ammonium chloride.

13. A method of conditioning hair comprising:
(I) wetting hair;
(II) applying to the hair an optically clear hair conditioning composition comprising:
  (A) an aminofunctional silicone microemulsion having an average particle size of less than 0.14 microns comprising:
    (i) an aminofunctional polyorganosiloxane having its formula selected from the group consisting of
    $R_3SiO(R_2SiO)_x(RQSiO)_ySiR_3$ and
    $HOR_2SiO(R_2SiO)_x(RQSiO)_ySiR_2OH$
    wherein R selected from the consisting of aryl, alkyl, and alkenyl radicals, Q is a polar radical having the formula —R'NHR² wherein R' is a divalent linking group composed of carbon and hydrogen atoms having from 2 to 10 carbon atoms, and R² is selected from the group consisting of a hydrogen atom, alkyl radicals containing from 1 to 4 carbon atoms, and the —CH₂CH₂NH₂ radical, the value of y is at least one, and the sum of x+y is less than 500;
    (ii) a surfactant which is insoluble in the polyorganosiloxane; and
    (iii) water; and
  (B) at least one long-chain dialkyl quaternary amine salt; and
  (C) water;
(III) massaging the optically clear hair conditioning composition into the hair; and
(IV) rinsing the optically clear hair conditioning composition from the hair with water.

14. A method according to claim 13, wherein R is methyl, Q is a polar radical having the formula —R'NHCH₂CH₂NH₂, R' is selected from the group consisting of propylene, and —CH₂CH(CH₃)CH₂—.

15. A method according to claim 13, wherein (B) is selected from the group consisting of ditallow dimethyl ammonium chloride, ditallow dimethyl ammonium methyl sulfate, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium chloride, dihexadecyl dimethyl ammonium acetate, ditallow dipropyl ammonium phosphate, ditallow dimethyl ammonium nitrate, di(coconutalkyl dimethyl ammonium chloride, stearyl dimethyl benzyl ammonium chloride, ditallow dimethyl ammonium chloride, dicetyl dimethyl ammonium chloride, stearyl dimethyl benzyl ammonium chloride, and dicoco dimethyl ammonium chloride.

* * * * *